United States Patent [19]

Cheng

[11] Patent Number: 5,858,805
[45] Date of Patent: Jan. 12, 1999

[54] ASSAY FOR AMINOGLYCOSIDE ANTIBIOTICS

[75] Inventor: Charles Minnan Cheng, Bridgewater, N.J.

[73] Assignee: Roche Diagnostic Systems, Inc., Branchburg, N.J.

[21] Appl. No.: 782,361

[22] Filed: Jan. 13, 1997

Related U.S. Application Data

[60] Provisional application No. 60/011,153 Jan. 26, 1996.
[51] Int. Cl.⁶ .................................................. G01N 33/542
[52] U.S. Cl. .......................... 436/537; 436/815; 436/826
[58] Field of Search ..................................... 436/537, 815, 436/826

[56] References Cited

U.S. PATENT DOCUMENTS

| | | | |
|---|---|---|---|
| 4,492,762 | 1/1985 | Wang et al. | 438/537 |
| 5,079,234 | 1/1992 | McGregor et al. | 514/789 |
| 5,393,659 | 2/1995 | Noah et al. | 435/7.94 |

FOREIGN PATENT DOCUMENTS

| | | |
|---|---|---|
| 0 372 413 A | 6/1990 | European Pat. Off. . |
| 0 388 961 A | 9/1990 | European Pat. Off. . |
| WO 96/09549A | 3/1996 | WIPO . |

OTHER PUBLICATIONS

M. Jolley at al., Clin. Chem., vol. 27, No. 7, pp. 1190–1197, 1981.
Dardliker and Feigen, Biochem. Biophys. Res. Comn. 5:299 (1961)
Geddes, et al., Chemother. 20:245–256 (1974)
Derwent Abstract AN 90–179672/24

*Primary Examiner*—Mary E. Ceperley
*Attorney, Agent, or Firm*—George W. Johnson; Patricia S. Rocha-Tramaloni

[57] ABSTRACT

This invention is directed to the use of polycarboxylic acid polymers to enhance the performance of immunochemical assays for the quantitation of aminoglycoside antibiotics in biological samples. This invention is also concerned with the improved homogeneous, immunochemical detection assays resulting from the use of said polycarboxylic acid polymers in said assays.

6 Claims, 2 Drawing Sheets

Improvement in assay response for amikacin calib.
Curve using PAA (0.15%)

Signal span between 20-40 ug/mL:  no PAA:    11.7 mP
                                  with PAA:  21.6 mP Improvement in assay response for gentamicin calib.
Curve using PAA (0.05%)

Signal span between 7.4-14 ug/mL:   no PAA:    11.6 mP
                                    with PAA:  17.8 mP Improvement in assay response for tobramycin calib.
Curve using PAA (0.0189%)

Signal span between 7-10 ug/mL:   no PAA:     5.7 mP
                                  with PAA:  10.3 mP Improvement in assay response for amikacin calib.
Curve using PMAA (0.178%)

Signal span between 20-40 ug/mL:  no PMAA:    11.1 mP
                                  with PMAA:  21.4 mP

ASSAY FOR AMINOGLYCOSIDE ANTIBIOTICS

This invention is directed to the use of polycarboxylic acid polymers to enhance the performance of immunochemical assays for the quantitation of aminoglycoside antibiotics in biological samples. This invention is also concerned with the improved homogeneous, immunochemical detection assays resulting from the use of said polycarboxylic acid polymers in said assays.

BACKGROUND OF THE INVENTION

Diagnostic assays for the detection of various substances ("analytes") in clinical specimens (e.g. plasma, serum, urine) are well known. These clinical diagnostic assays can be divided generally into two systems: heterogeneous and homogeneous systems. Heterogeneous systems, for example ELISA (enzyme linked immunosorbent assay), typically involve the use of an analyte- or antibody-linked solid phase for signal generation and require the separation and washing of the solid phase to reduce non-specific binding to the solid phase or background signal in assay measurements. In contrast, homogenous systems, such as the COBAS® FP and COBAS® OnLine (Roche Diagnostic Systems, Inc., Branchburg, N.J.), TDx® FP (Abbott Laboratories, North Chicago, Ill.), EMIT™ (Syva Co., Palo Alto, Calif.), and CEDIA® (Microgenics Corp., Concord, Calif.), utilize only liquid reagents and the signal is generated directly from the mixture of reagents without any separation procedure. Because of their simplicity, homogeneous assays may be fully automated.

It is also known to include various additives in the washing buffer of heterogeneous immunoassays to enhance the performance of the assay. For example, U.S. Pat. No. 5,393,659 discloses the use of a water-soluble polymer containing carboxyl groups to improve the sensitivity of ELISA assays. These "enhancing" additives typically do not participate in the immunochemical reaction itself but rather facilitate the washing efficiency and reduce the non-specific binding to the solid phase thereby decreasing the background signal (i.e., a heterogenous system). These additives may also enhance the minimal readable concentration of analyte, i.e. improve the sensitivity of the assay. See, e.g., U.S. Pat. No. 5,393,659.

Turning to the analytes that are detected by immunochemical assays, aminoglycoside antibiotics are known to exhibit high potency and to have a broad-spectrum bactericidal action against both Gram-negative and Gram-positive organisms. However, they are also known to have a narrow therapeutic index, making their use hazardous, particularly in patients with impaired renal function. See M. Jolley, et al., Clin. Chem. 27(7):1190–1197 (1981); U.S. Pat. No. 5,079, 234. Thus, patients being treated with aminoglycoside antibiotics are closely monitored for concentration of these drugs in their serum. Id. Because of the high toxicity potential of these drugs, there is also a continuing effort to improve the performance and sensitivity of known assays for aminoglycoside antibiotics.

SUMMARY OF THE INVENTION

The invention results from the discovery that use of water soluble polycarboxylic acid polymers (and copolymers) of general formula

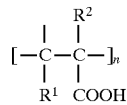

wherein $R^1$ is H or COOH,
$R^2$ is H or $CH_3$
and n is from 25 to 17,400 in known homogeneous immunological assays for the detection of aminoglycoside antibiotics significantly improves the overall performance of the assays.

DETAILED DESCRIPTION OF THE INVENTION

Figure 1A:
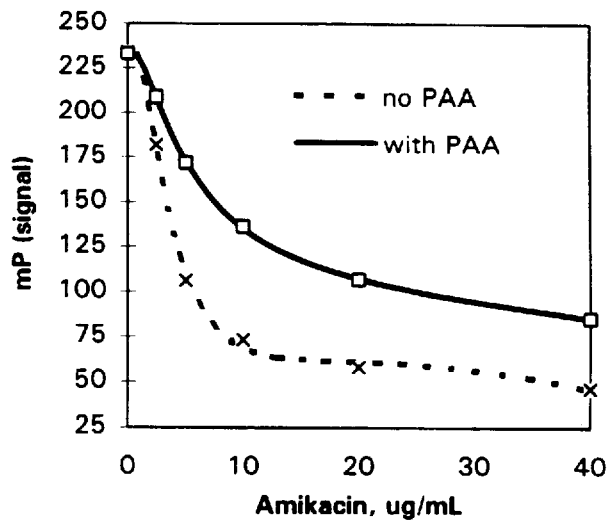
FIG. 1A demonstrates the improvement in the amikacin calibration curve when Poly(acrylic acid) (PAA) is added to a commercially available amikacin assay. This Figure is further described in Example 1.

In all immunoassays, a limited number of calibrators of known analyte (e.g., drug) concentration (most often 6 calibrators) are typically used to construct a non-linear standard curve for a particular analyte (drug). The calibrating curve is constructed for each particular instrument by using common mathematical equations known to those skilled in the art, such as equations describing an exponential 5 parameter relation, or logit/log 4 or logit/lot 5 relations. The specific equation for a particular instrument is typically provided in the manual accompanying the instrument. It is critical that the signals used to generate the curve (e.g. absorbance, fluorescence polarization, or bio/chemiluminescence) by any two adjacent calibrators be distinguishable so that the analyte concentration between these two calibrators can be determined accurately. Effective assay-response depends on differentiable signals for the different calibrators as well as a proper mathematical dose-response curve fit.

In current homogeneous immunoassays, particularly fluorescence polarization ("FP")-type assays, for aminoglycoside antibiotics such as amikacin, gentamicin, and tobramycin, the resulting calibration curves frequently demonstrate poor assay response (signal change per unit concentration of analyte), especially at the high end of the calibration curve, where the measured signal may be minimally differentiable. This is a serious limitation as the upper concentration range which is often of most interest for proper diagnostic monitoring often falls within this less precise portion of the curve. Thus, when such assays are used to determine aminoglycoside antibiotic concentrations at the higher concentration levels, less accurate results are often obtained.

Research into improving the performance characteristics of aminoglycoside antibiotic homogenous immunoassays has led to the discovery that use of water soluble polycarboxylic acid polymers of formula I

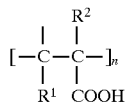

wherein $R^1$ is H or COOH, $R^2$ is H or $CH_3$ and n is from 25 to 17,400 in these assays significantly change the shape of the calibration curve and increase the dose-response for the higher analyte concentration of said assays, thereby providing an enhanced mathematical fit of an interpolated line to the limited number of calibrators used (e.g. 6). This shift in the calibration curve results in better assay accuracy and precision for analytes at higher concentration ranges than previously known.

As used herein "Soluble" or "water soluble Polycarboxylic acid polymers" refer to polymers (and copolymers) containing multiple carboxylic groups which are soluble in aqueous solution. It has been found that commercially available soluble polycarboxylic acid polymers of formula I having a molecular weight range of from about 1.8 KD (Kilo Daltons) to about 1250 KD improve the assay performance. Preferably, the molecular weight of the polymer is from about 1800 to about 225,000 Daltons.

Suitable polycarboxylic acid polymers of formula I for use in the present invention include polyacrylic acid ("PAA"), polymethacrylic acid ("PMAA"), polymaleic acid, and the corresponding copolymers of the foregoing polymers. PAA and PMAA are most preferred. These polymers are readily available commercially, for example from Aldrich Chemical Co. (WIS), Polysciences (PA), and Fluka (NY).

Aminoglycoside antibiotics which are detectable by the improved assay of this invention include amikacin, gentamicin, tobramycin, kanamycin, dibekacin and netilmicin.

The invention further relates to improved reagents for the detection of aminoglycoside antibiotics, the improvement comprising the inclusion of at least one polycarboxylic acid polymer of formula I in the reagent assembly or mix. Preferably, the polycarboxylic acid polymer is used as an independent reagent, but it could also be incorporated into the antibody reagent or other reagents of the immunoassay.

The minimal concentration of polycarboxylic acid polymer in the reagent mix that will result in improved assay performance varies from assay to assay, as well as from one type of antibody to another. The concentration of the polycarboxylic acid also depends on the type of polycarboxylic acid polymer used. For example, when PAA having a molecular weight of 20,000 Daltons is used, a concentration as small as 0.002% of the total reaction mixture was found sufficient to improve a tobramycin assay using a monoclonal antibody in the reagent mix. In an amikacin assay using polyclonal antibodies, a PAA (molecular weight 1800 daltons) concentration of 0.6% in the reaction mixture was required to achieve the desired assay performance. The determination of the ultimate concentration of a soluble polycarboxylic acid in the reaction mixture that is useful in a particular assay is well within the skill of the art in the immunoassay field. It is contemplated, however, that a final concentration of soluble polycarboxylic acid polymer in the reaction mixture of at least about 0.001% is useful in the methods of the present invention. Preferably, the soluble polycarboxylic acid polymer is present in a concentration of from about 0.002% to about 0.6% of the total reaction mixture.

The present invention is demonstrated on fluorescence polarization immunoassays (FPIA) performed on COBAS INTEGRA® and COBAS FARA II® (Roche Diagnostic Systems, Branchburg, N.J.) chemistry systems using the COBAS®-FP Reagents for each of amikacin, gentamicin and tobramycin. However, an FPIA according to the present invention also can be performed manually or on any type of automated system.

In FPIAs, fluorescence polarization is a reproducible function of the ligand (or drug) concentration, and is thus suitable for the quantitative determination of ligand (e.g. drug) concentrations in serum for the purpose of therapeutic drug monitoring.

It is well known to use fluorescence polarization in immunoassays to provide a quantitative means for measuring the amount of tracer-antibody conjugate produced in a competitive binding immunoassay. See, e.g., Dandliker and Feigen, Biochem. Biophys. Res. Comn. 5:299 (1961) and A. M. Geddes et al., Chemother. 20:245–256 (1974). In general, fluorescent polarization techniques are based on the principle that a fluorescein labeled compound when excited by linearly polarized light will emit fluorescence having a degree of polarization inversely related to its rate of rotation.

The COBAS®-FP systems use FP to measure the binding of fluorescein labeled drug (the "tracer") to specific antibodies. When tracer, serum containing antibodies specific for the drug to be measured, and drug-free patient serum are mixed together in the COBAS cuvette, most of the tracer binds to the antibodies. As a result, when the bound tracer is excited with polarized light (470–490 nm), the light emitted (510–530 nm) is highly polarized as the bound molecule cannot rotate and depolarize the light. On the other hand, if drug is present in the patient sample, the drug will compete with the tracer for binding to the antibodies. Thus, more of the tracer will remain unbound (and thus free to rotate) and the polarization of the emitted light will decrease.

The COBAS®-FP assay system measures the fluorescence polarization resulting from the interaction of tracer, antibody and calibrators containing known amounts of drug in human serum to produce a curve relating drug concentration to millipolarization (mP) units. Subsequently, the tracer, antibody and patient serum are allowed to interact under the same conditions which generated the calibration curve. The mP units thus obtained can be correlated to the drug level in the patient serum by comparison with the calibration curve in the assay.

From the standpoint of readability and accuracy, the steeper the slope of the calibration curve the easier it is to correlate drug concentration. Thus, those skilled in the art often refer to the concept of "span" for a particular drug measurement. "Span" or "delta value" is the signal difference between two specified analyte concentrations. A larger span in one area of the curve provides better precision for that particular region in an FPIA. However, at the same time, it is desirable to have a degree of overall uniformity in curve fit. Thus, achieving a very large signal span in one region of the curve is not desirable if this also results in a worse curve fit, that is poor reading accuracy, in another region of the curve. Therefore, to result in a reliable FPIA, a large signal span in one region has to be balanced with a relatively even distribution of "spans" throughout the entire calibration curve.

As is further demonstrated by the examples below, it has been found that the incorporation of soluble polycarboxylic acid polymers of formula I in the commercial sample/reagent mixture of a COBAS® chemistry analyzer changed the shape of the calibration curve such that the commercial assay performed more accurately over a wider range of analyte concentrations.

EXAMPLES

General Background

A. Materials

The following materials used in the examples were obtained from the following commercial sources:

a. polyacrylic acid (as a free acid or as a sodium salt) was obtained either from Polysciences (Warrington, Pa.), Fluka (Ronkonkoma, N.Y.), or Aldrich Chemical Co. (Milwaukee, Wis.);

b. polymethacrylic acid was obtained from Polysciences (Warrington, Pa.);

c. polymaleic acid was obtained from Polysciences (Warrington, Pa.)

d. the COBAS® products are available from Roche Diagnostic Systems, Inc. (Branchburg, N.J.).

B. Assay procedures

The assay protocols used in these examples were as follows. First antibody reagent, polycarboxylic acid solution, sample diluent and patient sample were added into a COBAS cuvette and the parallel and perpendicular fluorescence background intensities measured. The tracer was then added and the parallel and perpendicular fluorescence test intensities were then again measured. The polarization value was calculated by the automated analyzer (COBAS INTEGRA® or COBAS FARA II®) using the measured parallel and perpendicular test and background fluorescence intensities.

The COBAS INTEGRA® and FARA II® systems calculate the millipolarization (mP) units of a sample using the following formula:

$$mP = \frac{(I_{II\,TEST} - I_{II\,BLK} \cdot V_B/V_{TOT}) - k(I_{\perp TEST} - I_{\perp BLK} \cdot V_B/V_{TOT})}{(I_{II\,TEST} - I_{II\,BLK} \cdot V_B/V_{TOT}) + k(I_{\perp TEST} - I_{\perp BLK} \cdot V_B/V_{TOT})} \cdot 1000$$

$mP$ = Millipolarization units (polarization × 1000)
$I_{II\,BLK}$ = Parallel intensity of blank reading
$I_{II\,TEST}$ = Parallel intensity of test reading
$I_{\perp BLK}$ = Perpendicular intensity of blank reading
$I_{\perp TEST}$ = Perpendicular intensity of test reading
$V_B$ = Volume of the blank
$V_{TOT}$ = Volume of the test (total)
$k$ = Instrument adjust factor The systems calculate mP values for six calibrators and the applicable patient sample(s). The systems then calculate a best fit curve for the calibrators using a nonlinear least squares regression analysis. The concentration of drug in each sample is then interpolated from this curve using its measured polarization value.

In the following examples, the assays were performed as provided above with a particular polyacrylic acid being added as an independent reagent in the specific amounts indicated in each example.

Generally, the results of applicants examples are best understood in form of figures or tables and are thus so presented.

Example 1

Extension of Amikacin Calibration Curve by PAA

In Example 1, an assay for amikacin was performed using a commercially available COBAS®-FP Reagent kit for amikacin and adding PAA having a molecular weight of 20,000 Daltons. The concentration of PAA in the final reaction mix was 0.15%. As is shown in FIG. 1A, the signal span for the amikacin assay with added 0.15% PAA is significantly increased (from 11.7 mP to 21.6 mP) in the drug concentration range between 20 and 40 μg/mL. When the assay was performed without the addition of PAA (the broken line in FIG. 1A), the recovery of analyte beyond 25 μg/mL was less than optimal due to the narrow differentiable signal between the last two calibrators (at concentrations 20 μg/mL and 40 μg/mL). Once PAA was incorporated in the amikacin assay reagents, the reading accuracy for amikacin concentrations between 20 and 40 μg/mL improved dramatically due to an increase signal span between the 20 and 40 μg/mL calibrators, and the resulting overall curve fit was also improved. The improvement in the amikacin concentration curve in the range between 20–40 μg/mL is particularly significant inasmuch as the typical therapeutic range for amikacin is in fact between 20 and 30 μg/mL.

Example 2

Extension of Gentamicin Calibration Curve by PAA

Figure 1B:
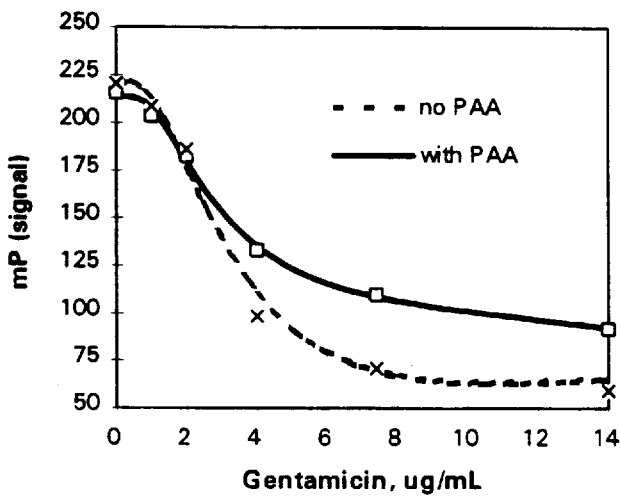
FIG. 1B demonstrates the improvement in the gentamicin calibration curve when PAA is added to a commercially available gentamicin assay. This Figure is further described in Example 2.

Similarly, in Example 2, an assay for gentamicin was performed using a commercially available COBAS®-FP Reagent kit for gentamicin and adding PAA having a molecular weight of 20,000 Daltons. The concentration of PAA in the final reaction mix was 0.05%. As is shown in FIG. 1B, the signal span for the gentamicin assay with added 0.05% PAA was significantly increased (from 11.6 mP to 17.8 mP) in the drug concentration range between 7.4 and 14 μg/mL. In contrast, when the assay was performed without the addition of PAA (the broken line in FIG. 1B), the calibration curve for the range 7.4–14 μg/mL was nearly a flat line (i.e. the curve had a very little slope making it very difficult to ascertain concentration differences). Once PAA was incorporated in the assay reagents, the reading accuracy for the gentamicin concentrations between 7.4 and 14 μg/mL (the last two calibrators) improved greatly due to an increase in the signal span, and so did the overall curve fit. The improvement in the gentamicin concentration curve in the range between 7.4–14 μg/mL is very significant inasmuch as the typical therapeutic range for gentamicin is from about 6 to about 10 μg/mL.

Example 3

Extension of Tobramycin Calibration Curve by PAA

Figure 2A:
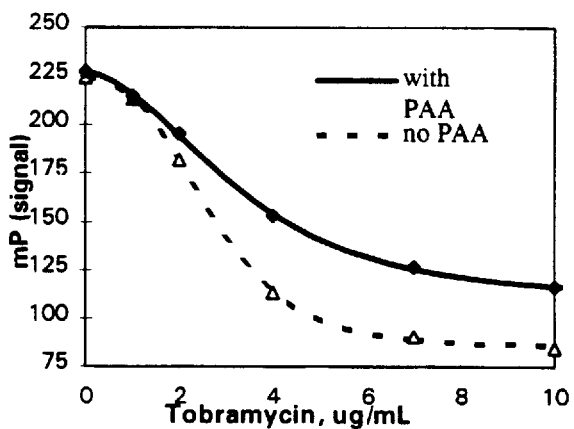
FIG. 2A demonstrates the improvement in the tobramycin calibration curve when PAA is added to a commercially available tobramycin assay. This Figure is further described in Example 3.

Analogous to Examples 1 and 2, in Example 3, an assay for tobramycin was performed using a commercially available COBAS®-FP Reagent kit for tobramycin and adding PAA having a molecular weight of 20,000 Daltons. The concentration of PAA in the final reaction mix was 0.0189%. As is shown in FIG. 2A, the signal span for the tobramycin assay with added PAA was vastly increased (from 5.7 mP to 10.3 mP) in the drug concentration range between 7 μg/mL and 10 μg/mL. Once again, the vast improvement in the tobramycin concentration curve in the range between 7–10 μg/mL is particularly significant as the typical therapeutic range for tobramycin is from about 6–10 μg/mL.

Example 4

Extension of Amikacin Calibration Curve by PMAA

Figure 2B:
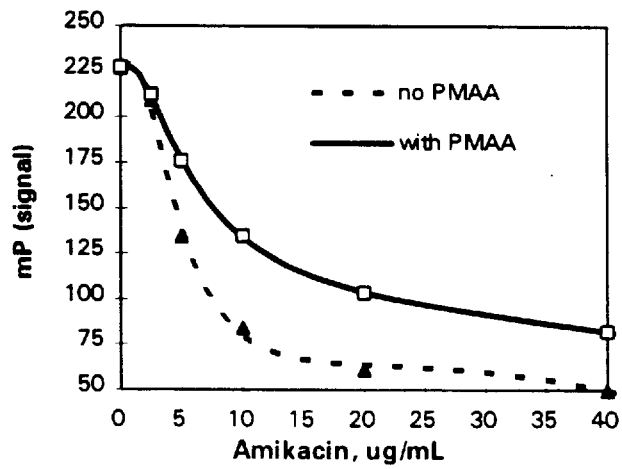
FIG. 2B demonstrates the improvement in the amikacin calibration curve when Poly(methacrylic acid) (PMAA) is added to a commercially available amikacin assay. This Figure is further described in Example 4.

In Example 4, an assay for amikacin was performed using a commercially available COBAS®-FP Reagent kit for amikacin and adding PMAA having a molecular weight of 15,000 Daltons. The concentration of PMAA in the final reaction mix was 0.178%. As is shown in FIG. 2B, the signal span for the amikacin assay with added PMAA is substantially increased (from 11.1 mP to 21.4 mP) in the drug concentration range between 20–40 μg/mL, which as is discussed above, is the key range for therapeutic monitoring of amikacin concentration.

Example 5

Improved Assay Accuracy for Amikacin Assay Using PAA

In this experiment, two standard curves using the measured signal from each of 6 calibrators having a known amikacin concentrations were constructed. The amikacin concentration of each calibrator is shown in Table I below. Both curves were generated using COBAS®-FP Reagent kits for amikacin. As noted in Table I, one curve was generated using standard reagents without PAA and the other curve was generated with PAA having been added to the reaction mix. The molecular weight of the PAA used in this experiment was about 20,000 Daltons, and the PAA concentration in the final reaction mix was 0.1%. All 6 calibrators were then assayed as unknown samples and the determined concentration for each was compared to the known concentration, and the deviation between the two concentrations for each calibrator was calculated. From a clinical standpoint, it is preferable to have a deviation in readings of less than 5% for each sample. As is shown below in Table I, a deviation in concentration measurements of less than 5% could not be achieved in the COBAS®-FP amikacin assay without added PAA. Rather, as is shown in Table I, at a concentration of about 20 μg/mL, the deviation in the concentration measurements was over 40%. However, when PAA was included in the reaction mix for the amikacin assay, the deviation in measured concentration throughout the entire length of the calibration curve was substantially reduced and, accordingly, the accuracy of the curve was much improved.

TABLE 1

Effect of Poly(acrylic acid) (PAA) [MW ~20,000] on the calibration curve fit (reading accuracy) of Amikacin assay.

| | Calibration Curve Fit in Assay Using | | | |
|---|---|---|---|---|
| | no PAA | | PAA (0.1% final conc.) | |
| Sample (μg/mL) | Found | Dev.(%) | Found | Dev.(%) |
| 0 | 0.91 | | 0.60 | |
| 2.5 | 2.38 | −4.8% | 2.44 | −2.4% |
| 5.0 | 5.28 | 5.6% | 5.13 | 2.6% |
| 10.0 | 8.81 | −11.9% | 9.72 | −2.8% |
| 20.0 | 28.91 | 44.5% | 20.49 | 2.5% |
| 40.0 | 39.40 | −1.5% | 39.84 | 0.4% |

Examples 6–10

In Examples 6–10, the same procedure was followed as described above in Example 5 for the amikacin assay, but using a PAA having a different molecular weight than that used in Example 5 or using PMAA instead of PAA. The results of Examples 6–10 are summarized below in Tables II–VI.

TABLE II

Effect of Poly(acrylic acid) (PAA) [MW 1,800] on the calibration curve fit (reading accuracy) of Amikacin assay.

| | Calibration Curve Fit in Assay Using | | | |
|---|---|---|---|---|
| | no PAA | | PAA (0.53% final conc.) | |
| Sample (μg/mL) | Found | Dev.(%) | Found | Dev.(%) |
| 0 | 0.64 | | 0.39 | |
| 2.5 | 2.43 | −2.8% | 2.47 | −1.2% |
| 5.0 | 5.25 | 5.0% | 5.08 | 1.6% |
| 10.0 | 8.70 | −13.0% | 9.77 | −2.3% |
| 20.0 | 27.40 | 37.0% | 20.46 | 2.3% |
| 40.0 | 39.49 | −1.3% | 39.85 | −0.4% |

TABLE III

Effect of Poly(acrylic acid) (PAA) [MW 225,000] on the calibration curve fit (reading accuracy) of Amikacin assay.

| | Calibration Curve Fit in Assay Using | | | |
|---|---|---|---|---|
| | no PAA | | PAA (0.05% final conc.) | |
| Sample (μg/mL) | Found | Dev.(%) | Found | Dev.(%) |
| 0 | 0.81 | | 0.58 | |
| 2.5 | 2.40 | −4.0% | 2.45 | −2.0% |
| 5.0 | 5.30 | 6.0% | 5.12 | 2.4% |
| 10.0 | 8.64 | −13.6% | 9.66 | −3.4% |
| 20.0 | 29.08 | 45.4% | 20.79 | 4.0% |
| 40.0 | 39.37 | −1.6% | 39.83 | −0.4% |

TABLE IV

Effect of Poly(acrylic acid) (PAA) [MW 1,250,000] on the calibration curve fit (reading accuracy) of Amikacin assay.

| | Calibration Curve Fit in Assay Using | | | |
|---|---|---|---|---|
| | no PAA | | PAA (0.009% final conc.) | |
| Sample (μg/mL) | Found | Dev.(%) | Found | Dev.(%) |
| 0 | 0.67 | | 0.55 | |
| 2.5 | 2.42 | −3.2% | 2.45 | −2.0% |
| 5.0 | 5.28 | 5.6% | 5.16 | 3.2% |
| 10.0 | 8.61 | −13.9% | 9.35 | −6.5% |
| 20.0 | 28.94 | 44.7% | 22.83 | 14.2% |
| 40.0 | 39.38 | −1.6% | 39.63 | −0.95 |

TABLE V

Effect of Poly(methacrylic acid) (PMAA) [MW ~15,000] on the calibration curve fit (reading accuracy) of Amikacin assay.

| | Calibration Curve Fit in Assay Using | | | |
|---|---|---|---|---|
| | no PMAA | | PMAA (0.177% final conc.) | |
| Sample (μg/mL) | Found | Dev.(%) | Found | Dev.(%) |
| 0 | 1.24 | | 0.79 | |
| 2.5 | 2.31 | −7.6% | 2.45 | −2.0% |
| 5.0 | 5.24 | 4.8% | 5.07 | 1.4% |
| 10.0 | 9.25 | −7.5% | 9.87 | −1.3% |
| 20.0 | 27.93 | 39.7% | 20.24 | 1.2% |
| 40.0 | 39.94 | −0.2% | 40.11 | 0.3% |

TABLE VI

Effect of Poly(maleic acid) (PMA) [Polysciences PMA, Catalog No. 09732] on the calibration curve fit (reading accuracy) of Amikacin assay.

| Sample (μg/mL) | Calibration Curve Fit in Assay Using | | | |
|---|---|---|---|---|
| | no PMA | | PMA (0.89% final conc.) | |
| | Found | Dev.(%) | Found | Dev.(%) |
| 0 | 0.74 | | 0.47 | |
| 2.5 | 2.41 | −3.6% | 2.45 | −2.0% |
| 5.0 | 5.28 | 5.6% | 5.20 | 4.0% |
| 10.0 | 8.58 | −14.2% | 9.16 | −8.4% |
| 20.0 | 29.88 | 49.4% | 23.41 | 17.1% |
| 40.O | 39.39 | −1.5% | 39.55 | −1.1% |

As in Example 5 and Table I, Examples 6–10 and Tables II–VI show that the addition of a commercially available soluble polycarboxylic acid polymer to the amikacin standard immunoassay results in much improved deviation in the drug concentration curve, and accordingly, improved assay accuracy.

Example 11

Improvement in Aminoglycoside Assay Precision at the High End of the Calibration Curve In Example 11, a sample of known amikacin concentration (21.5 μg/mL) was run in two separate experiments. For each assay, ten readings were made and the mean of these ten measurements is reported below in Table VII. The experiments were repeated and the same measurements made, but with PAA added to the reaction mix (0.15% final concentration of PAA of molecular weight 20,000).

In addition to reporting the mean concentration measured for each run, Table VII also reports the "coefficient of variation" (CV) for the sample, which is a measure of the discrepancy within the ten readings. The CV is obtained by taking the statistical variation of ten measurements and dividing by the mean. The coefficient of variation (i.e. "within-run" variation) is a measure of the precision obtained in a particular assay, that is, the ability to reproduce the results of the assay.

TABLE VII

Effect of PAA on the precision and accuracy as exemplified in the amikacin assay.

| | | Mean and Within-run C.V. of Sample in Assay Using | | | |
|---|---|---|---|---|---|
| | Amikacin | no PAA | | PAA | |
| Assay | Sample conc. (μg/mL) | Mean(10) | within-run C.V.(%) | Mean(10) | within-run C.V.(%) |
| Exp #1 | 21.5 | 25.82 | 8.0% | 21.72 | 2.40% |
| Exp #2 | 21.5 | 29.04 | 3.90% | 21.66 | 3.50% |

Table VII shows that at a sample concentration of 21.5 μg/mL, the accuracy of the amikacin assay is substantially improved by addition of PAA. This is evidenced by the readings of 25.82 and 29.04 (no PAA) contrasted with 21.72 and 21.66 (with PAA) for a known concentration of 21.5 μg/mL. In addition, Table VII also shows that the addition of PAA results in improved precision of the assay as measured by the coefficient of variation.

The above Examples were provided merely to illustrate the invention and are not intended to limit the scope of the invention.

What is claimed is:

1. In a homogeneous fluorescence polarization immunoassay for the determination of aminoglycoside antibiotics in a biological sample, the improvement comprising the use of a water-soluble polycarboxylic acid polymer of general formula

wherein $R^1$ is H or COOH,
$R^2$ is H or $CH_3$
and n is from 25 to 17,400 said polymer having a molecular weight of from about 1.8 KD to about 1250 KD.

2. The assay of claim 1 wherein the polycarboxylic acid polymer has a molecular weight of from about 1800 D to about 225,000 D.

3. In a homogeneous fluorescence polarization immunoassay for the determination of aminoglicoside antibiotics in a biological sample, the improvement comprising the use of a water-soluble polycarboxylic acid polymer having a molecular weight of from about 1800 D to about 1250 KD and being selected from the group consisting of polyacrylic acid, polymaleic acid, polymethacrylic acid, and copolymers thereof.

4. The assay of claim 3 wherein the polycarboxylic acid polymer is selected from polyacrylic acid and polymaleic acid.

5. The assay of claim 4 wherein the amount of water-soluble polycarboxylic acid polymer in the final assay reaction mix is at least 0.001%.

6. The assay of claim 5 wherein the amount of polycarboxylic acid polymer in the final reaction mix is from about 0.002% to about 0.6%.

* * * * *